United States Patent [19]
Mannschedel

[11] Patent Number: 6,162,056
[45] Date of Patent: *Dec. 19, 2000

[54] ANTIBACTERIAL COMPOSITION FOR FILLING ROOT CANALS AND METHOD FOR PREPARING THE SAME

[75] Inventor: Werner Mannschedel, Langenau, Germany

[73] Assignee: Roeko GmbH & Co., Dentalerzeugnisse, Germany

[ * ] Notice: This patent is subject to a terminal disclaimer.

[21] Appl. No.: 09/280,125

[22] Filed: Mar. 26, 1999

[30] Foreign Application Priority Data

Mar. 27, 1998 [DE] Germany ............................ 198 13 686

[51] Int. Cl.⁷ ...................................................... A61C 5/00
[52] U.S. Cl. ........................ 433/228.1; 433/226; 528/272
[58] Field of Search ................................ 433/226, 228.1; 528/272

[56] References Cited

PUBLICATIONS

U.S. application No. 09280125 Filing date Mar. 26, 1999.

*Primary Examiner*—Terressa M. Boykin
*Attorney, Agent, or Firm*—Brian J. Laurenzo; Michael C. Gilchrist

[57] ABSTRACT

The invention relates to a composition for filling root canals in humans or animals, comprising: (a) at least one chlorhexidine derivative of at least one carboxylic acid; (b) one or more carriers based on trans-polyisoprene, gutta-percha, balata, silicone, caoutchouc, acrylate, or mixtures thereof; (c) optionally one or more fillers; and (d) optionally one or more X-ray contrast substances.

21 Claims, No Drawings

ANTIBACTERIAL COMPOSITION FOR FILLING ROOT CANALS AND METHOD FOR PREPARING THE SAME

FIELD OF THE INVENTION

The present invention relates to an antibacterial composition, a method for preparing said antibacterial composition, and to the use of said antibacterial composition to fill root canals in humans or animals.

BACKGROUND ART

In order to treat a disorder known as pulpitis, the diseased pulpa is first removed mechanically from the root canal. Next, the root canal is cleaned, drilled out, and filled with an elastic-plastic element or with a different filling material. Finally, the root canal is sealed. Prior art illustrative of this process includes: Friedman et al. in J. Dent. Res., 54 (1975) 921–925; Briseno in Philipp J., 2, 90, 65–73; and U.S. Pat. No. 4,632,977. Suitable root canal filling materials, as described by Briseno, include inter alia semi-rigid cements based on synthetic resin, zinc oxide eugenol, calcium hydroxide or glass ionomer. U.S. Pat. No. 4,632,977 proposes filling materials based on trans-polyisoprene (for example, filling materials based on gutta-percha or balata). Gutta-percha points are commercially available in standard compositions that comprise: 20% by weight of gutta-percha matrix; from 60 to 75% by weight of zinc oxide filler; from 1 to 17% by weight of heavy metal sulphates that serve as X-ray contrast agents; and from 3 to 4% by weight of various waxes and resins that serve as softener. The aforementioned filling material is inert in the root canal and accordingly does not react with body tissue.

When a root canal has been filled with a known inert filling material, an inflammatory process may slowly develop after the filling operation (for example, as a result of germs remaining in the canal). The inflammation requires renewed treatment which often results in the complete loss of the tooth.

In response to this problem, compositions comprising antibiotics or calcium hydroxide have been used. Unfortunately, antibiotics have a large number of side-effects. For example, the use of antibiotics can result in the development of resistant bacterial strains. Therefore, the use of antibiotics is increasingly being rejected, especially for children.

The alternative use of calcium hydroxide is, in many cases, successful. However, it has recently been established that a number of bacteria, including *Streptococcus micros* and *Enterococcus faecalis,* are resistant to calcium hydroxide even at a pH value of 11. Therefore, these bacteria cannot be completely killed with calcium hydroxide.

U.S. Pat. Nos. 1,754,577 and 5,648,403 describe sealing root canals with a carrier comprising iodine-containing compounds. However, it has been recognized that a continuous release of iodine into the human body can result in deleterious side-effects and moreover that iodine compounds have an unattractive odor.

Iodine-containing and chlorhexidine-containing solutions for rinsing the oral cavity especially before, during and after surgical interventions, have also been disclosed. Illustrative examples of such disclosures include U.S. Pat. No. 4,738,840, U.S. Pat. No. 3,932,607, and the following foreign references: EP 94 102 340.0, RU 200 88 42, SU 165 0 138, and JP 622 65 225. In addition, the following references describe compositions comprising antibacterial compounds in a biodegradable or soluble carrier: EP 90 302 837.1 and WO 89/10 736.

The present invention solves many of the problems in the prior art by providing an anti-inflammatory composition for filling root canals in humans or animals that can be prepared and processed readily and simply. The present invention also provides a method of preparing such a composition.

SUMMARY OF THE INVENTION

The invention is a composition for filling root canals in humans or animals that comprises: at least one chlorhexidine derivative of at least one carboxylic acid; one or more carriers based on trans-poly-isoprene, gutta-percha, balata, silicone, caoutchouc, acrylate, or mixtures thereof; optionally one or more fillers; and optionally one or more X-ray contrast agents. The composition according to the invention may be used in the form of a temporary filling or, alternatively, as a permanent filling, of root canals in humans or animals.

In particular, the antibacterial composition according to the invention can be rolled, in the form of a powder or a liquid, into a carrier that substantially simplifies the preparation process. Alternatively, a carrier, for example a gutta-percha point, may be covered or surface-coated with the antibacterial composition. Preferably, the carrier comprises at least 80% by weight of trans-polyisoprene.

The composition according to the invention may be in the form of a gutta-percha point. The point may remain in the root canal temporarily, for example, for a few days. Alternatively, the point may remain in the root canal for a longer period of time or may be permanently left in the root canal.

Illustrative fillers include zinc oxide. When zinc oxide is employed it may be used either alone or in combination with one or more other customary fillers such as silicon dioxide, aluminum oxide, calcium hydroxide.

The composition according to the invention may additionally comprise one or more pharmaceutically active ingredients. Preferably, any pharmaceutically active ingredients are soluble or dispersible in an aqueous medium. In addition, the customary waxes, resins, and other auxiliaries, such as surfactants (e.g. polyethylene glycols, such as Dipluronic), may be employed in the invention.

DISCLOSURE OF THE INVENTION

The invention is an antibacterial composition comprising: (a) up to 99% by weight of carrier; (b) up to 99% by weight of filler; (c) from 0.01 to 50% by weight of at least one chlorhexidine derivative of at least one carboxylic acid; (d) up to 70% by weight of X-ray contrast agent, based on (a), (b) or (c); (e) up to 20% by weight of surfactants, (f) optionally additional customary components. All weight percentages given herein, unless otherwise specified, are based on the total weight of the composition.

Thus, the composition according to the invention is represented, for example, by a composition comprising: (a) up to 99% by weight of gutta-percha; (b) up to 99% by weight of zinc oxide as filler; (c) up to 50% by weight of a chlorhexidine derivative of at least one carboxylic acid; (d) up to 70% by weight of X-ray contrast agent, based on (a), (b) and (c); (e) from 0.01 to 20% by weight of surfactant; and (f) optionally additional customary components. Once again, all weight percentages given herein, unless otherwise specified, are based on the total weight of the composition.

As mentioned above, the composition according to the invention has the advantage that it can be used both as a temporary filling and as a permanent filling of root canals. When gutta-percha is used as the carrier, the carrier is neither eroded nor biodegraded. In contrast to the soluble or biodegradable carriers of the prior art, such compositions can thus remain in the mouth for any desired length of time without the root canal becoming re-infected.

If the root filling composition comprises, for example, approximately 5% by weight of an antibacterial agent according to the invention, such as chlorhexidine diacetate or chlorhexidine gluconate, that is homogeneously distributed in the gutta-percha point, and if the composition is introduced into a root canal, approximately 5% of the chlorhexidine derivative will dissolve. As a result, the total weight of the gutta-percha point will decrease by a maximum of 0.25%. With such a small decrease, no lesions occur that might allow re-infection of the root canal because the gutta-percha has plastic properties.

The composition according to the invention generally has four components. These four composition components, a method for making the composition, and an example of said composition, will be explained hereinafter in greater detail.

Component 1

The mechanical properties of the inventive composition for filling root canals are determined primarily by the properties of the carriers. The carriers can constitute from 35 to 60.0% by weight, preferably from 15 to 30% by weight, of the composition. The carriers should, on the one hand, be elastic so that they can be processed readily and introduced easily into the root canal. On the other hand, the carriers should also have plastic properties so that the root canal can be filled permanently without a gap remaining at the wall. Moreover, the carriers must be able to readily take up other components such as at least one antibacterial agent according to the invention and optionally a filler. For those purposes, a carrier comprising at least 80% by weight of trans-polyisoprene has proved advantageous. Gutta-percha may be mentioned by way of example. Gutta-percha is a naturally based carrier, the main component of which is trans-polyisoprene. Other trans-polyisoprenes may of course also be used, such as balata, as well as synthetic carriers based on isoprene, silicon, caoutchouc or acrylate, or various derivatives of the aforementioned materials. In the case of the gel-like compositions known from the prior art, it is difficult to achieve insertion into the apex and later to remove the necessarily temporary insert again.

Component 2

The composition according to the invention is characterized in that it comprises an antibacterial agent that includes at least one chlorhexidine (1,6-di-(4-chlorophenyldiguanido)-hexane) derivative of at least one carboxylic acid. Preferably, the antibacterial agent is a chlorhexidine derivative of only one or two carboxylic acids. The antibacterial agent is present in an amount of from 0.01 to 50% by weight, preferably in an amount from 0.01 to 25% by weight, more preferably in an amount from 0.1 to 15% by weight, even more preferably in an amount from 0.2 to 10% by weight, even more preferably in an amount from 0.3 to 5% by weight, and most preferably in an amount from 0.5 to 2.0% by weight, based on the weight of the total composition. The chlorhexidine derivatives are substances that are tolerated by both the tissue and the body and may be used in the form of a paste, aqueous solution, or powder. For example, they may be mixed with the carrier and compounded with further components, such as one or more fillers. Chlorhexidine derivatives of at least one carboxylic acid are, for example, chlorhexidine gluconate and chlorhexidine diacetate. Chlorhexidine diacetate is preferred.

The antibacterial agent can be rolled, for example, in the form of a powder or liquid or solution, into a carrier, such as gutta-percha. As a result, the preparation method can be greatly simplified.

Compared with the use of calcium hydroxide on its own, the composition according to the invention is additionally advantageous because it has a different spectrum of activity. Because no resistance develops, its acceptability compared with antibiotics is improved considerably.

Moreover, the composition of the instant invention can be left in the tooth permanently. In contrast, in the calcium hydroxide-containing compositions of the prior art, large amounts of calcium hydroxide are eroded. Unacceptable lesions would occur if the prior art compositions were used as a permanent insert.

Component 3

As the filler, customary fillers can generally be used. Preferred fillers include zinc oxide, silicon dioxide, aluminum oxide and calcium hydroxide. These fillers may be used alone or in combination. Calcium hydroxide is noted as being especially useful in the case of temporary fillings. The fillers are used in an amount of up to 99% by weight, preferably in an amount of from 10 to 70% by weight, and more preferably in an amount of from 15 to 40% by weight, based on the total weight of the composition.

Component 4

A further optional (although customary) component that may be utilized is an X-ray contrast agent. Suitable agents can be selected from the group consisting of zinc, ytterbium, yttrium, gadolinium, zirconium, strontium, tungsten, tantalum, niobium, barium, bismuth, molybdenum and lanthanum powders, powdered alloys thereof, oxides, fluorides, sulphates, carbonates, tungstates and carbides thereof. The X-ray contrast agent may be provided in an amount of up to 70% by weight, preferably from 10 to 60% by weight, and more preferably from 15 to 40% by weight, based on the total weight of compounds 1, 2 and 3.

The Method

The present invention also provides a method of preparing the above described composition filling root canals. The method comprises the following steps:

(a) forming a film of an isoprene-based carrier;

(b) optionally rolling into the carrier film one or more fillers and one or more X-ray contrast agents, surfactants and further optional customary auxiliaries, preferably in powder form or in a form that is not too highly viscous, (c) comminuting the compounded film and, preferably, in a manner known per se, extruding the product.

(d) cutting the extruded product and rolling the resulting cut pieces to form elastic-plastic elements suitable for filling root canals in humans and animals, wherein, in step (b), at least one antibacterial composition according to the invention is rolled into the carrier film, and/or wherein the film according to steps (b) or (c) or an element according to step (d) is covered or coated with a surface-coating or powder comprising at least one antibacterial composition.

Preferably, the temperature during extrusion rises from 50° C. to 120° C. More preferably, the temperature during extrusion rises from 60° C. to 110° C. This temperature rise results in a uniform germ-free product.

The following examples are intended to illustrate, but not limit, the invention:

EXAMPLE

To prepare gutta-percha points, a zinc oxide-containing gutta-percha matrix was first rolled between a carrier roller and a pressure roller, so that the gutta-percha lay around the carrier roller in the form of a thin film (like a skin). Then 8% by weight of chlorhexidine diacetate and 92% by weight of the gutta-percha-zinc oxide matrix were rolled into the film that had been produced. The film was then peeled away from the carrier roller. The peeled-away film was comminuted and extruded at a temperature rising from 60° C. to 110° C. to form a thin wire-like strand. That strand was then cut up and rolled.

What is claimed is:

1. A composition for filling root canals in humans or animals, comprising:
   (a) at least one chlorhexidine derivative of at least one carboxylic acid; and
   (b) at least one carrier selected from the group consisting of trans-polyisoprene, gutta-percha, balata, silicone, caoutchouc and acrylate.

2. The composition according to claim 1 further comprising at least one filler.

3. The composition according to claim 1 further comprising at least one X-ray contrast agent.

4. The composition according to claim 1, in which the carrier comprises at least 80% by weight of trans-polyisoprene.

5. The composition according to claim 1 in which the composition comprises a gutta-percha point.

6. The composition according to claim 2, wherein the filler is selected from the group consisting of zinc oxide, silicon dioxide, aluminum oxide and calcium hydroxide.

7. The composition according to claim 6 wherein the filler is a mixture of two or more fillers selected from the group consisting of zinc oxide, silicon dioxide, aluminum oxide and calcium hydroxide.

8. The composition according to claim 1 in which the carrier is primarily gutta-percha.

9. The composition according to claim 1, further comprising one or more waxes and/or resins.

10. The composition according to claim 1, further comprising a surfactant.

11. The composition according to claim 3, wherein the X-ray contrast agent is selected from the group consisting of zinc, ytterbium, yttrium, gadolinium, zirconium, strontium, tungsten, tantalum, niobium, barium, bismuth, molybdenum and lanthanum powders, powdered alloys thereof, oxides, fluorides, sulphates, carbonates, tungstates and carbides thereof.

12. The composition according to claim 1, further comprising a pharmaceutically active ingredient.

13. The composition according to claim 12, wherein said pharmaceutically active ingredient is soluble or dispersible in an aqueous medium.

14. The composition according to claim 3, further comprising:
   (a) up to 99.0% by weight of carrier;
   (b) up to 99% by weight of filler;
   (c) from 0.01 to 50% by weight of antibacterial agent;
   (d) up to 70% by weight of X-ray contrast agent, based on (a), (b) and (c); and
   (e) up to 20% by weight of surfactants,
wherein said percentages, unless otherwise specified, are based on the total weight of the composition.

15. The composition according to claim 14, further comprising:
   (a) up to 99% by weight of gutta-percha;
   (b) up to 99% by weight of zinc oxide as filler;
   (c) up to 50% by weight of antibacterial agent;
   (d) up to 70% by weight of X-ray contrast agent, based on (a), (b) or (c); and
   (e) from 0.01 to 20% by weight of surfactant,
wherein said percentages, unless otherwise specified, are based on the total weight of the composition.

16. A method of preparing a composition according to any one of the preceding claims, comprising the following steps:
   (a) forming a film of an isoprene-based carrier;
   (b) optionally rolling into the carrier film one or more fillers and optionally one or more X-ray contrast agents, surfactants and/or other auxiliaries; and
   (c) the film is formed into elastic-plastic elements suitable for filling root canals in humans and animals by an appropriate means,
wherein, in step (b), at least one antibacterial agent is rolled into the carrier film, and/or, in step (b) or (c), the film is covered or coated with a surface-coating or powder comprising at least one antibacterial agent.

17. The method according to claim 16, characterized in said means in step (c) includes comminuting and extruding the film in step (b), cutting the extruded product into separate pieces, and rolling each piece.

18. Method according to claim 17, characterized in that the temperature during extrusion rises from 50° C. to 120° C.

19. Method according to claim 18, characterized in that the temperature during extrusion rises from 60° C. to 110° C.

20. A temporary insert in root canals made with the composition in accordance with any one of claims 1 to 15.

21. A permanent filling in root canals made with the composition in accordance with to any one of claims 1 to 15.

* * * * *